US006839589B2

United States Patent
Petlan

(10) Patent No.: US 6,839,589 B2
(45) Date of Patent: Jan. 4, 2005

(54) METHOD AND APPARATUS FOR TREATMENT OF LIVING MATTER USING PULSED RADIO FREQUENCY ELECTROMAGNETIC RADIATION

(76) Inventor: Jiri Joseph Petlan, 4746 Caulfield Drive, West Vancouver, B.C. (CA), V7W 1G5

(*) Notice: Subject to any disclaimer, the term of this patent is extended or adjusted under 35 U.S.C. 154(b) by 233 days.

(21) Appl. No.: 09/960,971

(22) Filed: Sep. 25, 2001

(65) Prior Publication Data

US 2003/0060847 A1 Mar. 27, 2003

(51) Int. Cl.[7] .................................................. A61N 5/02
(52) U.S. Cl. ........................... 607/2; 607/50; 607/156
(58) Field of Search ............................. 607/50–52, 1–2, 607/154–156, 43, 54

(56) References Cited

U.S. PATENT DOCUMENTS 5,584,863 A * 12/1996 Rauch et al. .................. 607/2
5,800,458 A * 9/1998 Wingrove ...................... 607/2
6,421,562 B1 * 7/2002 Ross .............................. 607/2

* cited by examiner

Primary Examiner—Angela D. Sykes
Assistant Examiner—Roderick Bradford
(74) Attorney, Agent, or Firm—Oyen Wiggs Green & Mutala

(57) ABSTRACT

A method of electrotherapy for living matter such as humans, animals and plants is provided. The method involves providing a transmitter for generating a radiofrequency electromagnetic transmission from an antenna in the range of 10 to 50 megahertz, determining empirically the resonant frequency of said human, animal or plant to be treated and placing said human, animal or plant to be treated in the vicinity of the antenna at the resonant frequency for a sufficient period of time to provide the desired benefits.

6 Claims, 2 Drawing Sheets

METHOD AND APPARATUS FOR TREATMENT OF LIVING MATTER USING PULSED RADIO FREQUENCY ELECTROMAGNETIC RADIATION

TECHNICAL FIELD

The invention relates to methods of electrotherapy and the use of electromagnetic frequencies to treat living matter.

BACKGROUND

Pulsed electromagnetic energy has long been used to promote healing in humans. The DIAPULSE™ machine was developed as an improvement on the previous methods of diathermy which used electromagnetic energy to radiate heat deep into the human tissue. The goal of the DIAPULSE machine was to increase the strength of the electromagnetic field without generating increased heat in the tissue. This was accomplished by pulsing the electromagnetic field in very short pulses, referred to as "ultra-short wave therapy". High frequency electromagnetic waves could be applied with increased voltage without overly heating the patient's tissue by applying the waves in pulses of very short duration. This "athermapeutic" method was found to provide therapeutic benefits without generating significant heat in the living matter.

For example, U.S. Pat. No. 2,276,995 issued Mar. 17, 1942 discloses a pulse generating circuit for applying electromagnetic radiation to a patient wherein the frequency of the electromagnetic waves is about 25 megacycles per second, and the energy is applied in pulses having a duration of about 1/20000 of a second and a frequency of about 900 per second, so that the interval between pulses is at least 10 times the pulse duration.

One of the limitations of the Diapulse machine's athermapeutic method was the fact that government regulations severely limited the frequency at which such machines could operate so as to avoid interfering with radio and television broadcasts. Consequently the Diapulse machine was designed to operate at a fixed ham radio frequency of 27.12 megacycles. See U.S. Pat. No. 3,043,310 issued Jul. 10, 1962 and U.S. Pat. No. 3,181,535 issued May 4, 1965. A solid state version of the Diapulse machine is disclosed in U.S. Pat. No. 3,670,737 issued Jun. 20, 1972. The machine has been applied to the treatment of migraine headaches (U.S. Pat. No. 5,718,721 issued Feb. 17, 1998), and wound healing. The machines are typically operated at a pulse duration of 65 microseconds and frequency of 600 pulses per second.

It has been found that frequencies other than 27.12 megacycles are more effective for electrotherapy of living matter using pulsed electromagnetic frequencies, but that such frequencies vary according to the application and living matter. There remains a need for useful electrotherapy of living matter using pulsed electromagnetic frequencies at an optimally effective frequency.

SUMMARY OF INVENTION

A method of electrotherapy for living matter such as humans, animals and plants is provided. The method involves providing a transmitter for generating a radiofrequency electromagnetic transmission from an antenna in the range of 10 to 50 megahertz, determining empirically the resonant frequency of said human, animal or plant to be treated and placing said human, animal or plant to be treated in the vicinity of the antenna at the resonant frequency for a sufficient period of time to provide the desired benefits. Preferably the radiofrequency is in the range of 18 to 18.5 megahertz. Preferably the radiofrequency electromagnetic transmission is pulsed at an empirically determined frequency and duration of pulses, and the duration of the pulses is in the range from 0.001 seconds to 200 seconds.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
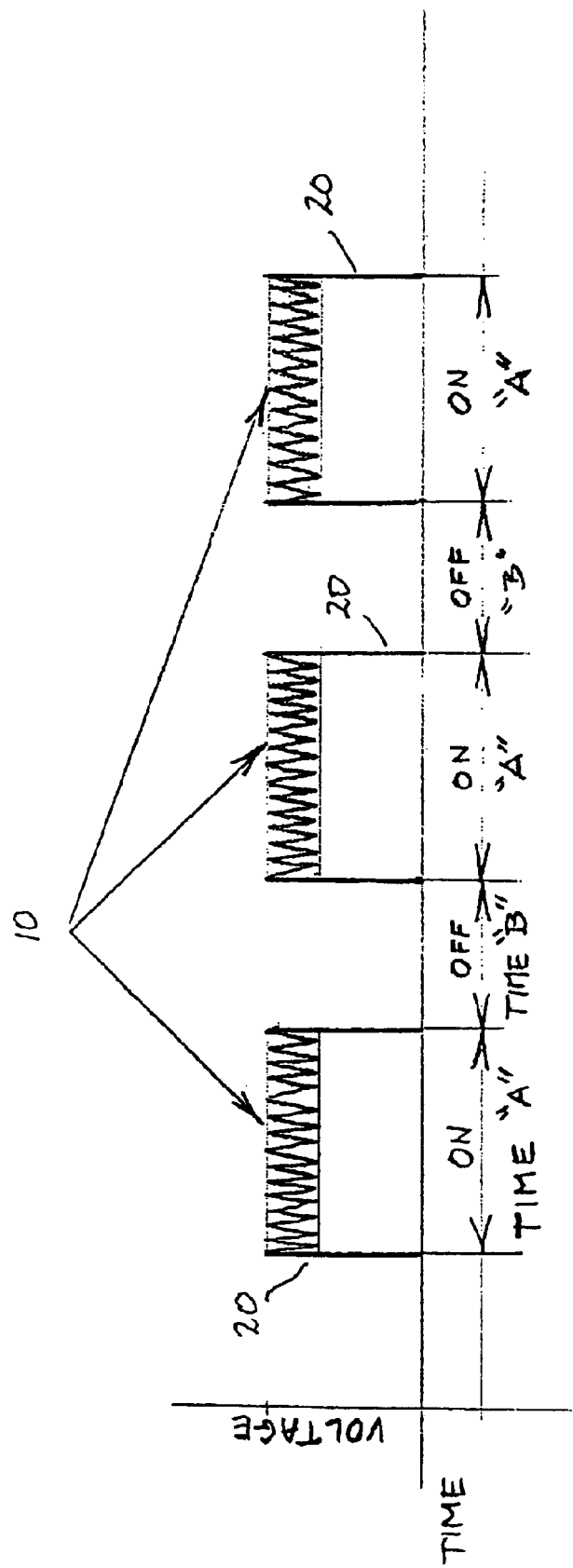
FIG. 1 is a pulse diagram illustrating the invention.
Figure 2:
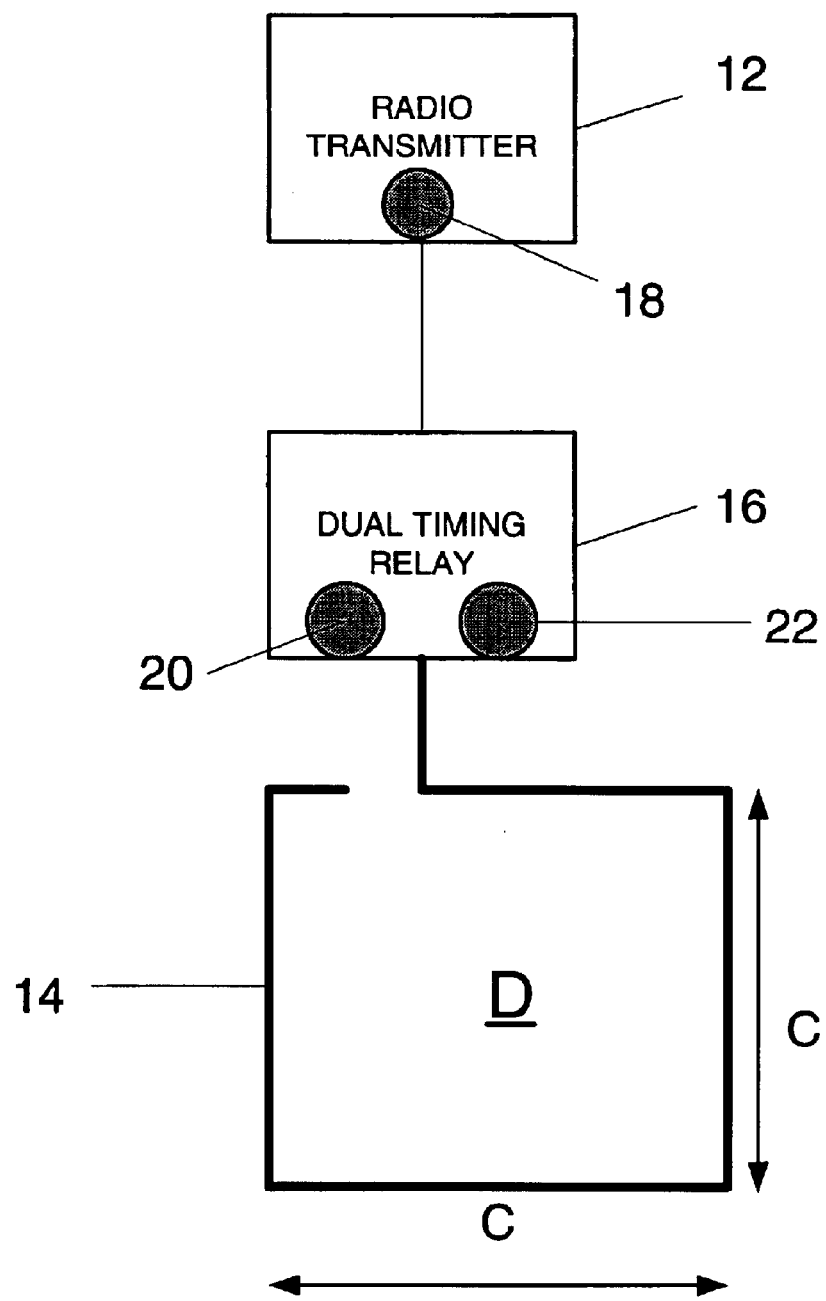
FIG. 2 is a block diagram illustrating a transmitter and antenna for use in the invention.

With reference to FIGS. 1 and 2, according to the present invention a radio frequency signal 10 is generated by radio transmitter 12. It has been found that for optimum treatment of any particular living matter, there is an optimum frequency within the range of 10 megahertz to 50 megahertz, referred to herein as the resonant frequency. For most humans the resonant frequency is in the range from 18 megahertz to 18.5 megahertz. The resonant frequency for any particular application is determined empirically in one of a number of ways. For example, in the case of a human, the human is placed in the electromagnetic field and reaction times of the human are tested at various frequencies of the field. This may be done, for example, by flashing a light in the human's eye and observing the reaction time for the pupil to react. The resonant frequency is then selected as the frequency at which the reaction time is quickest. Other known methods of measuring reaction time can also be used. While a particular resonant frequency may be optimum for certain treatments of that human, small variations from that frequency may be more effective to treat certain parts of that human's body, which can be determined empirically. Similarly for plants, the resonant frequency is determined empirically by placing the plant in the electromagnetic field and observing at which frequency optimum growth occurs. The resonant frequency for plants will generally be below 18 megahertz.

The radio frequency electromagnetic field may be achieved by a standard ham radio transmitter 12 transmitting through a quad antenna 14 having dimensions C of approximately 4 m. 21 cm on each side. A power output of 5 watts is sufficient for operation of the invention, although power of up to 500 watts output or more is also useful. The frequency is varied by frequency adjustment dial 18.

While the method of the invention works even if the radiofrequency field is not pulsed, the best results occur if the signal is pulsed. The high frequency electromagnetic transmission 10 may be pulsed by providing a timing relay 16 on the transmitter output. A double relay switch allows the pulse duration and frequency to be controlled. The pulse duration is varied by adjustment dial 20 and the pulse frequency (duration of spaces between pulses) is varied by adjustment dial 22. FIG. 1 illustrates the duration and frequency of the pulses 20. Period "A" is the duration of the pulse and period "B" is the duration between pulses. It has been found that the invention works with "A" and "B" from 0 to 10 hours but preferably from 0.001 seconds to 200 seconds. As in the case of the selection of the resonant frequency, the optimum pulse duration and frequency is selected empirically by placing the subject in the field and observing reaction time for humans or other animals or growth rate for plants while varying the pulse duration and frequency.

To obtain the benefits of the invention, the subject living matter (whether human, animal or plant) is preferably placed within the area D in FIG. 2, either in the same plane as antenna 14 or in a plane above or below the plane of antenna 14. The length of time the subject is subjected to the radiation, the power applied to the transmitter, the duration and frequency of the pulses are selected according to the desired application. The invention has the following useful applications:

Accelerating the healing and growth of skin in burn victims.

Regeneration of nerve connections in spinal injuries.

Healing of wounds.

Regeneration of deteriorating internal organs.

Restoration of eye sight from retinal damage or cataracts.

Promotion of hair growth.

Dissolving blood clots in the brains of stroke victims.

Regeneration of damaged heart tissue.

Healing of arthritic joints.

Improvement of skin condition such as reduction of liver spotting.

Stimulation of plant growth.

Reduction of disease or bug infestation in plants.

Healing of broken bones.

Reduction of tumors.

Regulating blood pressure.

Increasing brain activity.

Restoration of hearing.

Generally enhancing physical and mental performance in individuals including speed, endurance, strength and reaction time.

Thus, unlike the DIAPULSE machine, it has been discovered that the electrotherapy using radiofrequency electromagnetic waves can be done in a broad range of radio frequencies and a broad range of pulse durations and frequencies, and that improved results can be obtained by locating particular radio frequencies and pulse durations and frequencies depending on the application and type of living matter.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of electrotherapy for living matter such as humans, animals and plants comprising providing a transmitter for generating a radiofrequency electromagnetic transmission from an antenna in the range of 10 to 50 megahertz, determining empirically the resonant frequency of said human, animal or plant to be treated by placing said human, animal or plant to be treated in the vicinity of the antenna at a plurality of frequencies in said range and observing said human, animal or plant at each said frequency, and subsequently placing said human, animal or plant to be treated in the vicinity of the antenna at said resonant frequency pulsed at a pre-determined frequency and duration of pulses at a sufficient level of power and for a sufficient period of time to provide the desired benefits.

2. The method of claim 1 wherein said radiofrequency electromagnetic transmission is in the range of 18 to 18.5 megahertz.

3. The method of claim 1 wherein said radiofrequency electromagnetic transmission is pulsed at an empirically determined frequency and duration of pulses wherein said frequency and duration of said pulses are determining empirically by placing said human, animal or plant to be treated in the vicinity of the antenna at a plurality of pulse durations and frequencies and observing said human, animal or plant at each said pulse duration and frequency.

4. The method of claim 1 wherein said duration of said pulses is in the range from 0 seconds to 10 hours.

5. The method of claim 1 wherein said duration of said pulses is in the range from 0.001 seconds to 200 seconds.

6. The method of claim 1 wherein said electrotherapy is used for accelerating the healing and growth of skin in burn victims.

* * * * *